US00PP32730P2

(12) United States Plant Patent
Capo

(10) Patent No.: US PP32,730 P2
(45) Date of Patent: Jan. 5, 2021

(54) ***PETUNIA* PLANT NAMED 'KLEPH19120'**

(50) Latin Name: *Petunia hybrida*
Varietal Denomination: KLEPH19120

(71) Applicant: Klemm+Sohn GmbH & Co. KG, Stuttgart (DE)

(72) Inventor: Antonella Capo, Latina (IT)

(73) Assignee: Klemm+Sohn GmbH & Co. KG, Stuttgart (DE)

( * ) Notice: Subject to any disclaimer, the term of this patent is extended or adjusted under 35 U.S.C. 154(b) by 0 days.

(21) Appl. No.: 16/866,972

(22) Filed: May 5, 2020

(51) Int. Cl.
*A01H 5/02* (2018.01)
*A01H 6/82* (2018.01)

(52) U.S. Cl.
USPC ..... Plt./356.13
CPC ..... *A01H 6/824* (2018.05)

(58) Field of Classification Search
USPC ..... Plt./356.13
CPC ..... A01H 6/824
See application file for complete search history.

(56) References Cited

PUBLICATIONS

UPOV hit on *Petunia* plant named, 'KLEPH19120', QZ PBR 20201054, application date Apr. 22, 2020.*

* cited by examiner

*Primary Examiner* — Anne Marie Grunberg
(74) *Attorney, Agent, or Firm* — Weatherly IP Solutions, LLC; James Weatherly

(57) ABSTRACT

A new *Petunia* plant particularly distinguished by having a violet flower color with a well-defined white border, is disclosed.

1 Drawing Sheet

Genus and species: *Petunia hybrida.*
Variety denomination: 'KLEPH19120'.

BACKGROUND OF THE NEW PLANT

The present invention comprises a new and distinct variety of *Petunia*, botanically known as *Petunia hybrida* and hereinafter referred to by the variety name 'KLEPH19120'. 'KLEPH19120' is a selection from a cross-pollination of the proprietary female *Petunia* line 'PH-2014-0310' (unpatented) and the proprietary male *Petunia* line 'PH-2014-0316' (unpatented).

In July of 2014, the proprietary female *Petunia* line 'PH-2014-0310' and the proprietary male *Petunia* line 'PH-2014-0316' were cross pollinated in Latina, Italy and seeds were obtained. The seeds were sown and plants were grown for evaluation. A plant line was selected in April 2015 in Latina, Italy and named 'KLEPH19120'. In May 2015, 'KLEPH19120' was first vegetatively propagated by terminal tip cuttings and tissue culture in Latina, Italy. 'KLEPH19120' was found to reproduce true to type in successive generations of asexual propagation via tissue culture and terminal tip cuttings.

SUMMARY

The following are the most outstanding and distinguishing characteristics of this new variety when grown under normal horticultural practices in Latina, Italy.

1. Violet flower color with well-defined white border.

DESCRIPTION OF THE PHOTOGRAPH

This new *Petunia* plant is illustrated by the accompanying photograph, which shows a close-up of the flower of the plant. The plant is about 11 weeks old grown in Stuttgart, Germany in June 2019. The colors shown are as true as can be reasonably obtained by conventional photographic procedures.

DESCRIPTION OF THE NEW VARIETY

The following detailed descriptions set forth the distinctive characteristics of 'KLEPH19120'. The data which define these characteristics were collected from asexual reproductions carried out in Latina, Italy. Data was collected on fourteen-week-old plants grown indoors in Latina, Italy under greenhouse conditions in March 2020. Color references are to The R.H.S. Colour Chart of The Royal Horticultural Society of London (R.H.S.), 5$^{th}$ edition (2007).

Classification:
*Family.*—Solanaceae.
*Species.*—*Petunia hybrida.*
*Common name.*—*Petunia.*
*Variety.*—'KLEPH19120'.

Parentage:
*Female.*—Proprietary *Petunia* line 'PH-2014-0310'.
*Male.*—Proprietary *Petunia* line 'PH-2014-0316'.

Plant:
*Form and habit.*—Medium vigour plant with semi trailing habit.
*Height (from top of soil).*—Up to 10.0 cm.
*Width (horizontal plant diameter).*—Up to 30.0 cm.
*Propagation.*—Vegetative by terminal tip cuttings and tissue culture.
*Time to produce a finished flowering plant.*—About 13 weeks in winter under short day conditions, about 7 weeks in spring.
*Time to initiate and develop roots.*—2 to 3 weeks.

*Root description*.—Moderate density, moderate branching, white roots.

Stems:

*Average number* (*basal*).—About 5.0 cm.

*Length of basal branches* (*from the base of the stem to the tip*).—About 18.0 cm.

*Internode length*.—Up to 2.0 cm.

*Diameter of branches* (*from midpoint*).—About 0.4 cm.

*Stem color*.—RHS 144A.

*Anthocyanin*.—Absent.

*Texture*.—Pubescent.

Leaves:

*Arrangement*.—Slightly alternate along the stem, opposite under the inflorescence.

*Length*.—Up to 6.0 cm.

*Width*.—Up to 3.5 cm.

*Shape*.—Elliptic.

*Apex*.—Obtuse.

*Base*.—Attenuate.

*Margin*.—Entire.

*Immature leaf color*.—Upper surface: RHS N137B. Lower surface: RHS 138A.

*Mature leaf color*.—Upper surface: RHS N137D. Lower surface: RHS 138B.

*Texture*.—Upper surface: Pubescent. Lower surface: Pubescent.

*Venation pattern*.—Arcuate.

*Venation color*.—Upper surface: RHS N137B. Lower surface: RHS 143C.

*Petioles*.—Length: Up to 0.6 cm. Diameter: Up to 0.5 cm. Color: RHS 145B. Texture: Pubescent.

Flower bud:

*Shape*.—Irregularly oblong.

*Length*.—Up to 4.5 cm.

*Diameter*.—0.7 cm.

*Color at tight bud*.—RHS N92A and RHS 2D at the tip.

*Texture*.—Pubescent.

Inflorescence:

*Blooming habit* (*flowering season*).—Continuously flowering during spring and summertime.

*Inflorescence type*.—Sympodial, with monochasial growth.

*Number of flowers per node*.—1.

*Lastingness of individual blooms on the plant*.—About 10 days.

*Fragrance*.—Not detected.

*Flowers*.—Arrangement: Composed of 5 fused petals. Diameter (flower face): Up to 6.5 cm. Depth (total length of flower): Up to 7.0 cm. Throat/Funnel: Length: About 3.0 cm. Diameter (at opening): About 1.0 cm. Texture: Inner surface: Smooth. Outer surface: Pubescent. Color: Inner surface: RHS N92A. Outer surface: RHS 79B with a vein RHS N92A. Petals: Color, mature flower (fully opened): Upper surface: Closest to RHS 86A with an NN155C border. Lower surface: RHS N87A with an NN155C border. Apex: Truncate. Base: Fused. Shape: Salverform. Margin: Entire. Strength of waviness: Absent or very weak. Degree of lobation: Medium.

*Calyx arrangement*.—5 sepals fused at the base.

*Sepals*.—Color: Upper surface: RHS N137B. Lower surface: RHS 137C. Length: Up to 1.8 cm. Width: Up to 0.7 cm. Shape: Oblong/spatulate. Apex: Broadly acute. Base: Attenuate. Margin: Entire. Texture: Upper surface: Pubescent. Lower surface: Pubescent.

*Pedicels*.—Color: RHS 144A. Length: Up to 2.5 cm. Diameter: About 0.2 cm. Texture: Pubescent.

Reproductive organs:

*Stamens*.—Quantity: 5. Shape: Needle with oblong head. Filament: Length: Up to 1.4 cm. Diameter: 0.05 cm. Color: RHS 157C. Anther: Shape: Oblong. Color: RHS 85A to RHS 85D. Length: 0.25 cm. Diameter: 0.2 cm. Pollen: Color: RHS 91A. Amount: Abundant.

*Pistils*.—Quantity per flower: 1. Length: 2.7 cm. Stigma color: RHS 139A. Style color: RHS 145A.

Fruit and seed set: None observed.

Disease and pest/insect resistance: None observed.

COMPARISON WITH PARENTAL LINES AND KNOWN VARIETY

'KLEPH19120' is a distinct variety of *Petunia*. 'KLEPH19120' is distinguished from its parents as described in Table 1:

TABLE 1

Comparison with Parental Lines

| Trait | Variety 'KLEPH19120' | Female parent 'PH-2014-0310' | Male Parent 'PH-2014-0316' |
|---|---|---|---|
| Flower color | Violet with well defined white border | Purple with white border | Magenta purple with white, less defined, border |

'KLEPH19120' is most similar to the commercial *Petunia* plant named 'KLEPH09189' (U.S. Plant Pat. No. 21,916). Differences between the two varieties are described in Table 2:

TABLE 2

Comparison with Similar Variety

| Characteristic | Variety 'KLEPH19120' | Commercial line 'KLEPH09189' |
|---|---|---|
| Flower color | Violet with well defined white border | Magenta purple with white border |

I claim:

1. A new and distinct variety of *Petunia* plant named 'KLEPH19120' as illustrated and described herein.

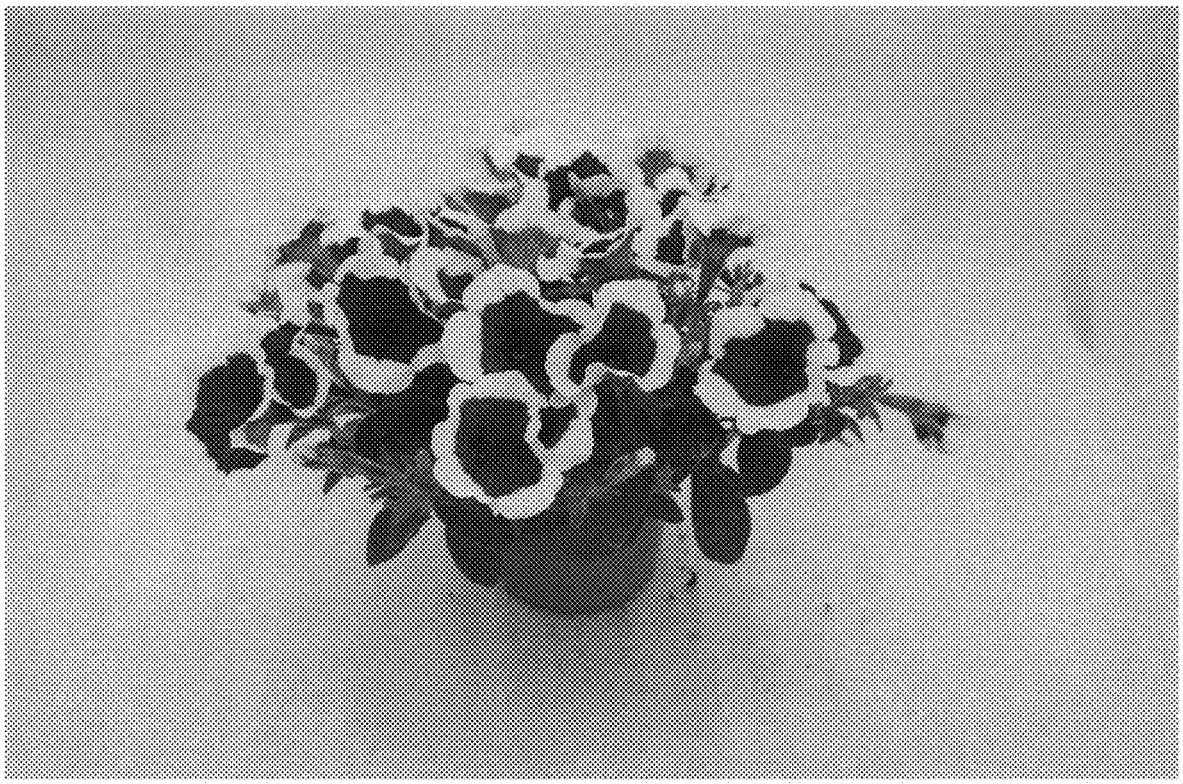

* * * * *